US00RE34277E

United States Patent [19]

Denis et al.

[11] E Patent Number: Re. 34,277

[45] Reissued Date of Patent: Jun. 8, 1993

[54] PROCESS FOR PREPARING TAXOL

[75] Inventors: Jean-Noel Denis; Andrew E. Greene, both of Uriage; Daniel Guenard, Montrouge; Francoise Gueritte-Voegelein, Les Ulis, all of France

[73] Assignee: Centre National de la Recherche Scientifique, Paris, France

[21] Appl. No.: 786,871

[22] Filed: Nov. 1, 1991

Related U.S. Patent Documents

Reissue of:

[64] Patent No.: 4,924,011
Issued: May 8, 1990
Appl. No.: 331,807
Filed: Apr. 3, 1989

[51] Int. Cl.[5] ..... C07D 305/14; C07F 7/02

[52] U.S. Cl. ..... 549/510; 549/419; 549/420; 549/510; 549/511; 549/214

[58] Field of Search ..... 549/214, 510, 511, 419, 549/420

[56] References Cited

U.S. PATENT DOCUMENTS 4,814,470 3/1989 Colin et al. ..... 549/510
4,857,653 8/1989 Colin et al. ..... 549/510

FOREIGN PATENT DOCUMENTS 253738 7/1987 European Pat. Off. .
253739 7/1987 European Pat. Off. .

OTHER PUBLICATIONS

"Modified Taxols, 4.[1] Synthesis and Biological Activity of Taxols Modified in the side chain", J. Natural Products, vol. 51, pp. 298-306 (1988).

"Taxol and Derivatives: A Biogenetic Hypothesis", Journal of Natural Products, vol. 50, No. 1, pp. 9-18, 1987, Gueritte-Voegelein, et al.

Relationships between the structures of taxol and baccatine III derivatives and their in vitro action on the disassembly of mammalian brain and Physarum amoebal microtubules, Proc. Natl. Acad. Sci., U.S.A. vol. 81, pp. 4090-4094, Jul. 1984, Lataste, et al.

"Application of the Vicinal Oxyamination Reaction with Assymmetric Induction to the Hemisynthesis of Taxol and Analogues", Tetrahedron, vol. 45, No. 13, pp. 4177 to 4190, 1989, Mangatal, et al.

"A Highly Efficient, Practical Approach to Natural Taxol", Journal American Chemical Society, 1988, vol. 110, pp. 5917-5919, Denis, et al.

"Biologically Active Taxol Analogues with Deleted A-Ring Side Chain Substituents and Variable C-2'Configurations", J. Med. Chem. 1991, vol. 34, pp. 1176-1184, Swindell, et al.

J. Org. Chem., vol. 51, pp. 46-50, 1986 "An Efficient, Enantioselective Synthesis of the Taxol Side Chain".

*Primary Examiner*—C. Warren Ivy
*Assistant Examiner*—Ba K. Trinh
*Attorney, Agent, or Firm*—Morgan & Finnegan

[57] ABSTRACT

Process for preparing taxol by the condensation of a (2R, 3S) acid of general formula (I) with a taxan derivative of general formula (II), followed by the removal of the groups $R_2$ and $R_3$ protecting the hydroxy groups *and intermediates used therein.*

(II)

(I)

17 Claims, No Drawings

PROCESS FOR PREPARING TAXOL

Matter enclosed in heavy brackets [ ] appears in the original patent but forms no part of this reissue specification; matter printed in italics indicates the additions made by reissue.

The present n relates to a process for preparing taxol from a derivative of 10-deacetylbaccatine III or baccatine.

Among taxan derivatives which correspond to the general formula:

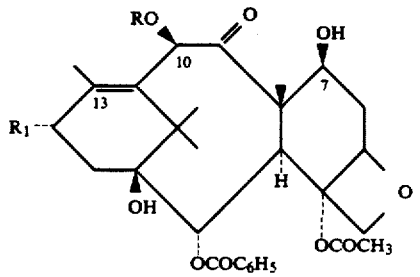

(I)

taxol is that for which R denotes an acetyl radical and $R_1$ denotes a (2'R,3'S) —OCO—CHOH—CH($C_6H_5$)—NH$COC_6H_5$ radical, 10-deacetylbaccatine III is that for which R denotes a hydrogen atom and $R_1$ denotes a hydroxy radical and baccatine III is that for which R denotes an acetyl radical and $R_1$ denotes a hydroxy radical.

Whereas taxol exhibits noteworthy properties in vitro as a promoter of tubulin polymerization and as an inhibitor of tubule depolymerization, and as a result constitutes an especially important antileukaemic and antitumour agent, 10-deacetylbaccatine III and baccatine III do not manifest these activities.

Taxol and baccatine III are extracted with difficulty and in generally low yields, of the order of 100 mg/kg in the case of taxol, from the trunk barks of different Taxus species.

Baccatine III is found in larger amounts in the wood of these different plant species.

In contrast, 10-deacetylbaccatine III is extracted much more readily and in better yields (300 mg/kg of leaves) from yew leaves.

A process enabling taxol to be prepared from 10-deacetylbaccatine III, which is readily accessible and whose production does not necessitate the total destruction of the plant species, is hence especially advantageous.

In European Patent Application EP No. 253,739, the preparation was described of taxol and 10-deacetyltaxol from a taxan derivative of general formula:

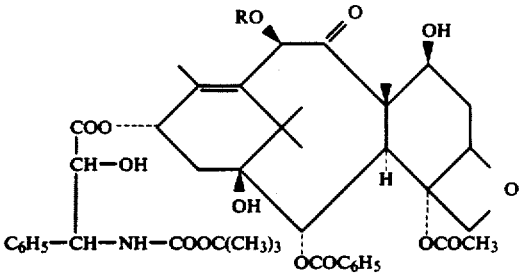

(II)

The preparation of this from baccatine III or from 10-deacetylbaccatine III, forms the subject of European Patent Application EP No. 253,738, and necessitates the intermediate separation of the diastereoisomers. As a result, it is impossible for all the baccatine III or 10-deacetylbaccatine III introduced to yield taxol having the appropriate configuration.

The present invention provides a process for preparing taxol of formula:

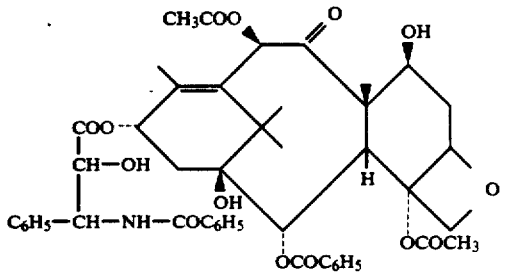

in which a (2R, 3S) 3-phenylisoserine derivative of general formula:

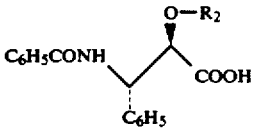

(III)

in which $R_2$ is a hydroxy-protecting group, is esterified with a taxan derivative of general formula:

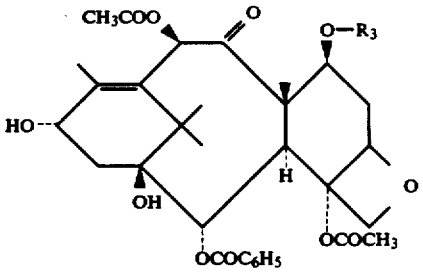

(IV)

in which $R_3$ is a hydroxy-protecting group, and the protecting groups $R_2$ and $R_3$ are then both replaced by hydrogen.

This process may be used to produce taxol in good yield from a starting material which is easily obtained in quantity.

In the general formula (III), $R_2$ denotes, more especially, a methoxymethyl, 1-ethoxyethyl, benzyloxymethyl, (β-trimethylsilylethoxy)methyl, tetrahydropyranyl or 2,2,2-trichloroethoxycarbonyl radical. Preferably, $R_2$ is a 1-ethoxyethyl radical.

In the general formula (IV), $R_3$ denotes, more especially, a trialkylsilyl radical in which each alkyl portion contains 1 to 3 carbon atoms. Preferably, $R_3$ is a trimethylsilyl or triethylsilyl radical It is especially advantageous to use a product of general formula (IV) in which $R_3$ denotes a triethylsilyl radical.

In general, the esterification of the taxan derivative of general formula (IV) with the acid of general formula (III) is performed in the presence of a condensing agent, for example a carbodiimide such as dicyclohexylcarbodiimide or a reactive carbonate such as di-2-pyridyl carbonate, and an activating agent, for example a dialkylaminopyridine such as 4-dimethylaminopyridine, working in an aromatic solvent such as benzene, toluene, a xylene, ethylbenzene, iospropylbenzene or chlorobenzene at a temperature of between 60° and 90° C.

In general, an excess of acid of general formula (III) and of condensing agent (dicyclohexylcarbodiimide, di-2-pyridyl carbonate) is used, preferably 6 to 10 moles of each per mole of taxan derivative of general formula (IV), and at least one mole, and preferably 2 to 4 moles, of activating agent (4-dimethylaminopyridine) per mole of taxan derivative of general formula (IV).

The removal of the groups protecting the (2'R,3,S) ester obtained, of general formula:

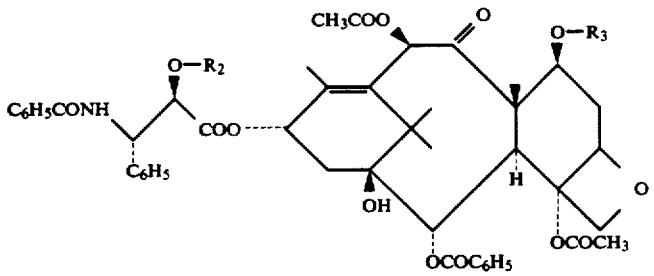

(V)

in which $R_2$ and $R_3$ are defined as above, is generally accomplished by treatment in an acid medium. It is especially advantageous to use an acid such as hydrochloric acid, dissolved in an aliphatic alcohol containing 1 to 3 carbon atoms (methanol, ethanol, propanol, isopropanol) at a temperature in the region of 0° C.

The product of general formula (III) may be obtained by the saponification of a (2R, 3S) ester of general formula:

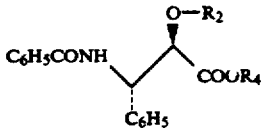

(VI)

in which $R_2$ is defined as above and R denotes an alkyl group containing 1 to 4 carbon atoms, and preferably methyl, by means of an inorganic base such as an alkali metal hydroxide (lithium hydroxide, sodium hydroxide) or an alkali metal carbonate or bicarbonate (sodium bicarbonate, potassium carbonate), in an aqueousalcoholic medium such as an ethanol/water or methanol/water mixture, working at a temperature of between 10° and 40° C. and preferably in the region of 25° C.

The product of general formula (VI) may be obtained under the usual conditions for preparation of ethers, and more especially according to the processes described by J. N. Denis et al., J. Org. Chem., 51, 46–50 (1986).

The product of general formula (IV) may be obtained by the action of a halotrialkylsilane on baccatine III or on 10-deacetylbaccatine III, followed, in the latter case, by the acetylation of the intermediate 7-trialkylsilyl-10-deacetylbaccatine III obtained.

In general, the reaction of the halotrialkylsilane with baccatine III or with 10-deacetylbaccatine III is performed at a temperature in the region of 20° C., working in a basic organic solvent such as pyridine or in an inert organic solvent such as chloroform or dichloroethane in the presence of a tertiary amine such as triethylamine, Hünig's base or pyridine.

The acetylation of the 7-trialkylsilyl-10-deacetylbaccatine III is generally accomplished by means of acetyl chloride, working at a temperature in the region of 0° C. in a basic organic solvent such as pyridine or in an inert organic solvent such as methylene chloride, chloroform or dichloroethane in the presence of a tertiary amine such as pyridine or Hünig's base.

The example which follows, given without implied limitation, shows how the invention can be put into practice.

EXAMPLE 42.8 mg (0.12 mmol) of N-benzoyl-O-(1-ethoxyethyl)-3-phenylisoserine in 1 $cm^3$ of anhydrous toluene are introduced under an argon atmosphere into a 5-$cm^3$ round-bottomed flask equipped with a magnetic stirrer. 25.9 mg (0.12 mmol) of di-2-pyridyl carbonate are then added. The mixture is left to react for 4 to 5 minutes, and 4.9 mg (0.04 mmol) of 4-dimethylaminopyridine and 14 mg (0.02 mmol) of 7-triethylsilylbaccatine III are then added in a single portion. The colourless and homogeneous solution is left for 3 to 4 minutes, and then heated for 10 hours at 72°–74° C. After being cooled, the reaction mixture is diluted by adding ethyl acetate. The organic solution is washed 3 times with saturated aqueous sodium bicarbonate solution, twice with water and then twice with saturated sodium chloride solution. The organic phase is dried over anhydrous sodium sulphate. After filtration and removal of the solvents under reduced pressure (20 mm of mercury; 2.7 kPa), the residue obtained is purified by analytical thin-layer chromatography on silica, eluting with an ether/methylene chloride (5:95 by volume) mixture, 4 runs being performed. 8.4 mg (0.0081 mmol) of ester of general formula (V) in which $R_2$ denotes a 1-ethoxyethyl radical and $R_3$ denotes a triethylsilyl radical is thereby obtained, in a 40% yield, in the form of a mixture of 2 epimers in the ratio 60:40, melting at 169°–173° C. after recrystallization in a methylene chloride/pentane mixture.

5.8 mg of 7-triethylsilylbaccatine III are recovered. The ester obtained has the following characteristics:

optical rotation: $[\alpha]^{24}=-33.7°$ (c=0.41; methanol)

infrared spectrum (film): 3450, 3300, 3060, 3025, 2950, 2930, 2900, 2870, 1740, 1720, 1640, 1600, 1580, 1520, 1480, 1450, 1365, 1310, 1260, 1240, 1175, 1140, 1105, 1090, 1080, 1020, 980, 945, 820 and 710 $cm^{-1}$ proton nuclear magnetic resonance spectrum (300 MHz; deuterated chloroform; chemical shift in ppm; coupling constants J in Hz):

0.53–0.62 (m, 6H); 0.93 (t, J=8, 9H); 1.00 (t, J=7, less abundant epimer 3H); 1.04 (t, J=7, preponderant epimer 3H); 1.18 (preponderant epimer) and 1.19 (less abundant epimer) (2s, 3H); 1.22 (s, 3H); 1.20 and 1.29 (2d, J=5.3, 3H); 1.70 (s, 3H); 1.85–1.95 (m, 1H); 2.00 and 2.01 (2d, J=1.2, 3H); 2.05–2.20 (m, 1H); 2.16 (s, 3H); 2.26–2.40 (m, 1H); 2.40 (preponderant epimer) and 2.53 (less abundant epimer) (2s, 3H); 2.46–2.59 (m, 1H); 3.04–3.44 (m, 2H); 3.81 (preponderant epimer) and 3.83 (less abundant epimer) (2d, J=7, 1H); 4.24 (less abundant epimer) and 4.26 (preponderant epimer) (2ABq, $J_{AB}=8.1$, $\delta_A-\delta_B=34$, 2H); 4.47 (dd, J=6.6 and 10.6, 1H); 4.64 (less abundant epimer) and 4.72 (preponderant epimer) (2d, J=2.7 and 3.7, 1H); 4.54 (less abundant epimer) and 4.80 (preponderant epimer) (2q, J=5.3, 1H); 4.94 (ps.-t, J=6.7 and 7.3, 1H); 5.68–5.76 (m, 2H); 6.24 (ps.-t, J=8 and 9, 1H); 6.44 (s, 1H); 7.08 (less abundant epimer) and 7.18 (preponderant epimer) (2d, J=8.6 and 8.1, 1H); 7.28–7.53 (m, 10H); 7.57–7.63 (m, 1H); 7.77–7.80 (m, 2H); 8.10–8.15 (m, 2H)

mass spectrum (FAB; NBA matrix): m/e=1040 ($MH^+$)

elemental analysis: $C_{57}H_{73}O_{15}SiN$

| elemental analysis: $C_{57}H_{73}O_{15}SiN$ | | | |
|---|---|---|---|
| Calculated % | C 65.81 | H 7.07 | N 1.35 |
| Found | 65.57 | 7.34 | 1.62 |

72 mg (0.009 mmol) of the ester obtained above are introduced at 0° C. under an argon atmosphere into a 10-$cm^3$ round-bottomed flask equipped with a magnetic stirrer. 3.6 $cm^3$ of a 0.5% strength ethanolic hydrochloric acid solution, cooled beforehand to 0° C., are added. The mixture is stirred at 0° C. for 30 hours. When the reaction is complete, the reaction mixture is diluted by adding ethylacetate at 0° C., and water is then added. After settling has taken place, the separated organic phase is washed 5 times with water and twice with saturated sodium chloride solution and is then dried over anhydrous sodium sulphate. After filtration, the solvents are removed under reduced pressure (20 mm of mercury; 2.6 kPa). The residue obtained (72 mg) is purified by preparative thinlayer chromatography on silica, eluting with a dichloromethane/methanol (90:10 by volume) mixture. 54 mg (0.063 mmol) of taxol are thereby obtained.

The yield is 91%.

The taxol thereby obtained has the following characteristics:

optical rotation: $[\alpha]^{24}=-49.7°$ (c=0.36; methanol)

infrared spectrum (film): 3400, 3060, 3025, 3000, 2950, 2900, 1740, 1720, 1650, 1600, 1580, 1520, 1480, 1450, 1370, 1315, 1260, 1240, 1180, 1110, 1070, 1030, 980, 950, 905, 800 and 710 $cm^{-1}$ proton nuclear magnetic resonance spectrum (300 MHz; deuterated chloroform; chemical shifts in ppm; coupling constants in Hz):

1.15 (s, 3H); 1.24 (s, 3H); 1.69 (s, 3H); 1.80 (s, 3H); 1.83 (s, 1H); 1.83–1.93 (m, 1H; 2.24 (s, 3H); 2.28–2.39 (m, 2H); 2.39 (s, 3H); 2.47 (d, J=4, 1H); 2.48–2.57 (m, 1H); 3.55 (d, J=5, 1H); 3.80 (d, J=7, 1H); 4.25 (ABq, $J_{AB}=8.4$, $\delta_A-\delta_B=32$, 2H); 4.37–4.44 (m, 1H); 4.80 (dd, J=2.5 and 5, 1H); 4.95 (d, J=7.7, 1H); 5.68 (d, J=7, 1H); 5.79 (dd, J=2.5 and 8.8, 1H); 6.23 (t, J=9, 1H); 6.27 (s, 1H); 6.98 (d, J=8.8, 1H); 7.33–7.54 (m, 10H); 7.59–7.64 (m, 1H); 7.72–7.75 (m, 2H); 8.12–8.15 (m, 2H)

$^{13}C$ nuclear magnetic resonance spectrum (deuterated chloroform):

9.57 ($CH_3$); 14.83 ($CH_3$); 20.83 ($CH_3$); 21.62 ($CH_3$); 22.85 ($CH_3$); 26.69 ($CH_3$); 35.65 ($CH_2$); 35.73 ($CH_2$); 43.20 (C); 45.86 (CH); 55.05 (CH); 58.67 (C); 72.20 (CH); 72.41 (CH); 73.23 (CH); 75.00 (CH); 75.58 (CH); 76.58 ($CH_2$); 79.10 (C); 81.21 (C); 84.42 (CH); 127.06 (CH); 128.38 (CH); 128.72 (CH); 129.04 (CH); 129.21 (C); 130.22 (CH); 131.97 (CH); 133.26 (C); 133.71 (CH); 138.03 (C); 141.98 (C); 167.04 (C); 170.37 (C); 171.22 (C); 172.73 (C); 203.62 (C)

mass spectrum (FAB; NBA matrix): m/e=854 ($MH^+$).

(2R, 3S)-N-Benzoyl-O-(1-ethoxyethyl)-3-phenylisoserine may be obtained in the following manner:

380 mg of N-benzoyl-O-(1-ethoxyethyl)-3-phenylisoserine methyl ester are added into a 100 $cm^3$ round-bottomed flask equipped with a magnetic stirrer and containing 30 $cm^3$ of methanol. To the solution obtained, 15 $cm^3$ of distilled water and 414 mg (3 mmol) of solid potassium carbonate are added. The mixture is stirred for 40 hours at 25° C. and the methanol is then evaporated off under reduced pressure. The residual aqueous phase is extracted several times with ether. The aqueous phase is acidified with 10% strength (w/v) aqueous hydrochloric acid solution and then extracted with dichloromethane. The combined organic phases are washed several times with water and then with saturated sodium chloride solution. The organic phases are dried over anhydrous magnesium sulphate. After filtration and removal of the solvent under reduced pressure, 254 mg (0.711 mmol) of N-benzoyl-O-(1-ethoxyethyl)-3-phenylisoserine are obtained, the characteristics of which are as follows:

melting point: 93°–94° C.

infrared spectrum (film): 3425, 3600–2100, 3060, 3025, 2950, 2925, 1740, 1640, 1600, 1580, 1520, 1480, 1440, 1300, 1140, 1075, 1020, 950, 920, 865, 800, 770 and 700 $cm^{-1}$ proton nuclear magnetic resonance spectrum (300 MHz; deuterated chloroform; chemical shifts in ppm; coupling constants J in Hz): 0.90 and 1.07 (2t, J=7, 3H); 1.24 (d, J=5.3, 3H); 2.88–2.99 and 3.24–3.45 (2m, 2H); 4.50 and 4.63 (2d, J=2.4, 1H); 4.60 and 4.81 (2q, J=5.3, 1H); 5.74–5.80 (m, 1H); 7.26–7.52 (m, 4H); 7.48–7.83 (m, 2H); 7.0–7.8 (broad s, 1H).

(2R, 3S)-N-Benzoyl-O-(1-ethoxyethyl)-3-phenylisoserine methyl ester may be prepared in the following manner:

2.99 mg (1 mmol) of N-benzoyl-3-phenylisoserine methyl ester, 10 $cm^3$ of dry dichloromethane, 25.1 mg (0.1 mmol) of pyridinium p-toluenesulphonate and 956.4 μl (721 mg; 10 mmol) of ethyl vinyl ether are introduced successively into a 25-$cm^3$ round-bottomed flask equipped with a magnetic stirrer. The reaction mixture is stirred for 3 hours at 25° C. When the reaction is complete, 1 drop of pyridine is added and the reaction mixture is then diluted by adding dichloromethane. The organic phase is washed twice with water and then with saturated sodium chloride solution, and dried over anhydrous sodium sulphate. After filtration and removal of the solvents under reduced pressure, 380 mg of N-benzoyl-O-(1-ethoxy- ethyl)-3-phenylisoserine methyl ester are obtained in the form of an equimolecular mixture of 2 epimers, the characteristics of which are as follows:

melting point: 124°-125° C. (after recrystallization in a dichloromethane/pentane mixture)

optical rotation: $[\alpha]^{23}=-25.9°$ (c=0.54; methanol)

infrared spectrum (film): 3350, 3060, 3025, 2980, 2940, 1740, 1635, 1600, 1580, 1530, 1490, 1435, 1380, 1340, 1320, 1275, 1242, 1198, 1175, 1150, 1080, 1030, 990, 955, 900, 800, 702 and 698 $cm^{-1}$ proton nuclear magnetic resonance spectrum (300 MHz; deuterated chloroform; chemical shifts in ppm; coupling constants J in Hz):

0.87 and 0.98 (2t, J=7, 3H); 1.13 and 1.22 (2d, J=5.4, 3H); 2.82 and 2.89 and 3.22-3.36 (m, 2H); 3.755 and 3.76 (2s, 3H); 4.48 and 4.60 (2d, J=2.4, 1H); 4.50 and 4.78 (2q, J=5.4, 1H); 5.64 and 5.68 (2dd, J=2.4 and 8.2, 1H); 7.18 and 7.19 (2d, J=8.2, 1H); 7.23-7.55 (m, 8H); 7.80-7.84 (m, 2H)

mass spectrum (FAB, NBA matrix): m/e=372 ($MH^+$)

elemental analysis: $C_{21}H_{25}O_5N$

| elemental analysis: $C_{21}H_{25}O_5N$ | | | |
|---|---|---|---|
| Calculated % | C 67.90 | H 6.78 | N 3.77 |
| Found | 67.98 | 6.94 | 3.75 |

N-Benzoyl-3-phenylisoserine methyl ester may be prepared according to J. N. Denis et al., J. Org. Chem., 51. 46-50 (1986).

7-Triethylsilylbaccatine III may be repeated in one of the following ways:

(a) 544 mg (1 mmol) of 10-deacetylbaccatine III, dissolved in 50 $cm^3$ of anhydrous pyridine, are introduced under an argon atmosphere into a 100-$cm^3$ round-bottomed flask equipped with a magnetic stirrer. 3.36 $cm^3$ (3.014 g; 20 mmol) of triethylsilyl chloride are then added. The homogeneous, yellow reaction mixture is then stirred for 24 hours at 0° C. Ethyl acetate and water are then added. After settling has taken place, the separated aqueous phase is extracted with ethyl acetate. The combined organic phases are treated with saturated aqueous copper sulphate solution until the pyridine has been completely removed. The organic phases are washed with water and then with saturated sodium chloride solution, and then dried over anhydrous sodium sulphate. After filtration and evaporation of the solvents under reduced pressure, 2.73 g of a product are obtained, and this is purified on a silica column, eluting with a dichloromethane/methanol (99:1 by volume) mixture. 512 mg (0.778 mmol) of 10-deacetyl-7-triethylsilylbaccatine III are thereby obtained, in a 78% yield, in the form of a white solid, the characteristics of which are as follows:

melting point: 256°-257° C. (after recrystallization in a dichloromethane/pentane mixture)

optical rotation: $[\alpha]^{23}=-23.6°$ (c=0.41; methanol)

infrared spectrum (film): 3450, 2950, 2875, 1735, 1705, 1600, 1580, 1450, 1380, 1275, 1242, 1180, 1140, 1115, 1100, 1075, 1060, 1030, 1020, 1000, 990, 950, 925, 885, 860, 822, 740 and 715 $cm^{-1}$ proton nuclear magnetic resonance spectrum (300 MHz; deuterated chloroform; chemical shifts in ppm; coupling constants J in Hz):

0.48-0.70 (m, 6H); 0.94 (t, J=8, 9H); 1.08 (s, 6H); 1.57 (s, 1H); 1.74 (s, 3H); 1.86-1.95 (m, 1H); 2.02 (d, J=5, 1H); 2.09 (d, J=1.1, 3H); 2.25-2.35 (m, 2H); 2.28 (s, 3H); 2.42-2.52 (m, 1H); 3.95 (d, J=7, 1H); 4.24 (ABq, $J_{AB}=8.2$, $\delta_A-\delta_B=42$, 2H); 4.24 (d, J=2, 1H); 4.41 (dd, J=6.6 and 10.6, 1H); 4.85-4.90 (m, 1H); 4.95 (dd, J=1.9 and 9.6, 1H); 5.17 (d, J=2, 1H); 5.60 (d, L, J=7, 1H); 7.44-7.50 (m, 2H); 7.57-7.62 (m, 1H); 8.08-8.11 (m, 2H)

$^{13}C$ nuclear magnetic resonance spectrum (deuterated chloroform):

5.16 ($CH_2$); 6.72 ($CH_3$); 9.92 ($CH_3$); 15.13 ($CH_3$); 19.50 ($CH_3$); 22.60 ($CH_3$); 26.86 ($CH_3$); 37.26 ($CH_2$); 38.64 ($CH_2$); 42.70 (C); 46.99 (CH); 57.96 (C); 67.95 (CH); 72.95 (CH); 74.68 (CH); 74.83 (CH); 76.57 ($CH_2$); 78.78 (C); 80.75 (C); 84.25 (CH); 128.57 (CH); 129.44 (C); 130.07 (CH); 133.57 (CH); 135.20 (C); 141.78 (C); 167.04 (C); 170.76 (C); 210.31 (C)

mass spectrum (FAB; NBA matrix): m/e=659 (MH)

elemental analysis: $C_{35}H_{50}O_{10}Si$

| elemental analysis: $C_{35}H_{50}O_{10}Si$ | | | |
|---|---|---|---|
| Calculated % | C 63.80 | H 7.65 | Si 4.26 |
| Found | 63.57 | 7.72 | 4.04 |

43.9 mg (0.075 mmol) of 10-deacetyl-7-triethylsilylbaccatine III, dissolved in 1.87 $cm^3$ of anhydrous pyridine, are introduced under an argon atmosphere into a 10-$cm^3$ round-bottomed flask equipped with a magnetic stirrer. The solution is cooled to 0° C. and 26.6 μl (29.4 mg; 0.375 mmol) of acetyl chloride are then added dropwise. The mixture, which becomes heterogeneous, is stirred for 20 hours at 0° C. A further 26.6 μl of acetyl chloride are added and the mixture is then stirred for 20 hours at 0° C. Ethyl acetate is added, followed by water, at 0° C. After settling has taken place, the separated aqueous phase is extracted twice with ethyl acetate. The combined organic phases are washed with saturated aqueous copper sulphate solution until the pyridine has been completely removed, then with water and then with saturated sodium chloride solution, and are finally dried over anhydrous sodium sulphate. After filtration and removal of the solvents under reduced pressure, the residue obtained (65 mg) is purified by chromatography on a silica gel column, eluting with a dichloromethane/methanol (99:1 by volume) mixture. 45 mg (0.0643 mmol) of 7-triethylsilylbaccatine III are thereby obtained in an 86% yield, the characteristics of which are as follows:

melting point: 253°-254° C. (after recrystallization in a dichloromethane/pentane mixture)

optical rotation: $[\alpha]^{23}=-48.6°$ (c=0.36; methanol)

infrared spectrum (film): 3500, 2950, 2875, 1720, 1600, 1580, 1450, 1370, 1270, 1240, 1180, 1140, 1110, 1100, 1075, 1050, 1020, 990, 970, 950, 820 740 and 710 $cm^{-1}$ proton nuclear magnetic resonance spectrum (300 MHz; deuterated chloroform; chemical shifts in ppm; coupling constants J in Hz):

0.52-0.65 (m, 6H); 0.93 (t, J=8, 9H); 1.05 (s, 3H); 1.20 (s, 3H); 1.61 (s, 1H); 1.68 (s, 3H); 1.83-1.92 (m, 1H); 2.01 (d, J=5, 1H); 2.17 (s, 3H); 2.19 (d, J=1.1, 3H); 2.24-2.28 (m, 2H); 2.28 (s, 3H); 2.41-2.58 (m, 1H); 3.88 (d, J=7,

1H); 4.23 (ABq, $J_{Ab}=8.1$, $\delta_A-\delta_B=45$, 2H); 4.45 (dd, J=6.6 and 10.5, 1H); 4.83 (m, 1H); 4.96 (d, J=9.6, 1H); 5.63 (d, J=7, 1H); 6.46 (s, 1H); 7.45-7.50 (m, 2H); 7.57-7.63 (m, 1H); 8.09-8.12 (m, 2H)

$^{13}C$ nuclear magnetic resonance spectrum (deuterated chloroform): 5.28, 6.72; 9.93; 14.93; 20.06; 20.93; 22.68; 26.83; 37.24; 38.24; 42.79; 47.24; 58.67; 68.00; 72.35; 74.35; 75.77; 76.57; 78.73; 80.89; 84.22; 128.57; 129.38; 130.09; 132.78; 133.61; 143.83; 167.12; 169.33; 170.76 and 202.12 mass spectrum (FAB; NBA matrix): m/e=701 ($MH^+$)

elemental analysis: $C_{37}H_{52}O_{11}Si$

| elemental analysis: $C_{37}H_{52}O_{11}Si$ | | | |
|---|---|---|---|
| Calculated % | C 63.40 | N 7.48 | Si 4.01 |
| Found | 63.50 | 7.59 | 3.94 |

(b) 250 mg (0.4266 mmol) of baccatine III, dissolved in 8.5 $cm^3$ of anhydrous pyridine, are introduced under an argon atmosphere into a 25 $cm^3$ round-bottomed flask equipped with a magnetic stirrer. 1.43 $cm^3$ (1.286 g; 8.53 mmol) of triethylsilyl chloride are then added. The mixture is stirred for 28 hours at 20° C. Ethyl acetate is added, followed by water. After settling has occurred, the aqueous phase is extracted with ethyl acetate, the combined organic phases are washed with saturated aqueous copper sulphate solution until the pyridine has been completely removed, then with water and finally with saturated aqueous sodium chloride solution. The organic phases are dried over anhydrous sodium sulphate. After filtration and evaporation of the solvents under reduced pressure, a residue (1.35 g) is obtained, and this is purified by filtration on a silica gel column, eluting with dichloromethane/methanol (99:1 by volume) mixture. 248 mg (0.354 mmol) of 7-triethylsilyl baccatine III are thereby obtained, in an 83% yield, in the form of a white solid, melting at 253°-254° C. after recrystallization in a dichloromethane/pentane mixture.

We claim:

1. A process for preparing taxol of formula:

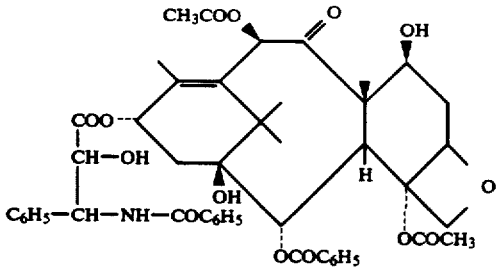

in which a (2R, 3S) 3-phenylisoserine derivative of general formula:

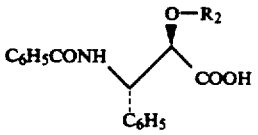

in which $R_2$ is a hydroxy-protecting group, is esterified with a taxan derivative of general formula:

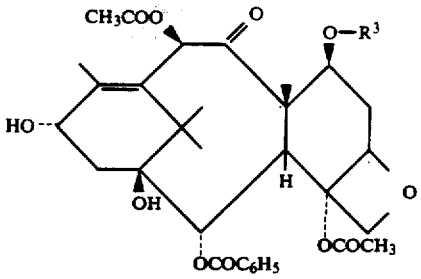

(II)

in which $R_3$ is a hydroxy-protecting group, and the protecting groups $R_2$ and $R_3$ are then both replaced by hydrogen.

2. A process according to claim 1, in which $R_2$ is chosen from methoxymethyl, 1-ethoxyethyl, benzyloxymethyl, (β-trimethylsilylethoxy)methyl, tetrahydropyranyl and 2,2,2-trichloroethoxycarbonyl, and $R_3$ is chosen from trialkylsilyl groups in which each alkyl portion contains 1 to 3 carbon atoms.

3. A process according to claim 2, in which the esterification is performed in the presence of a condensing agent and an activating agent.

4. A process according to claim 3, in which the condensing agent is chosen from carbodiimides and reactive carbonates, and the activating agent is chosen from dialkylaminopyridines.

5. A process according to claim 4, in which the condensing agent is chosen from dicyclohexylcarbodiimide and di-2-pyridyl carbonate and the activating agent is 4-dimethylaminopyridine.

6. A process according to claim 1, in which the reaction is performed in an aromatic organic solvent chosen from benzene, toluene, xylenes, ethylbenzene, isopropylbenzene and chlorobenzene.

7. A process according to claim 1, in which the reaction is performed at a temperature of between 60° and 90° C.

8. A process according to claim 1, in which the replacement of the protecting groups with hydrogen in the intermediate (2'R, 3'S) ester obtained, of general formula:

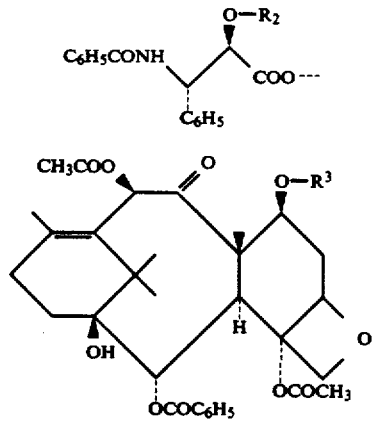

in which $R_2$ and $R_3$ are as defined in claim 1, is performed in an acid medium.

9. A process according to claim 8, in which the acid medium comprises and inorganic acid dissolved in an aliphatic alcohol containing 1 to 3 carbon atoms.

10. A process according to claim 9, in which the inorganic acid is hydrochloric acid.

11. A process according to claim 8, in which the reaction is performed at a temperature in the region of 0° C.

*12. A taxan derivative of the formula:*

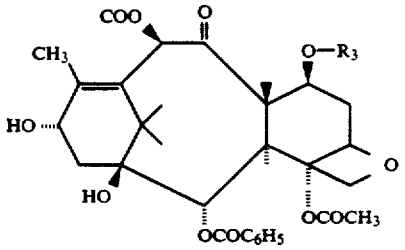

*wherein $R_3$ is a trialkylsilyl group in which each alkyl portion contains 1 to 3 carbon atoms.*

*13. A taxan derivative of the formula:*

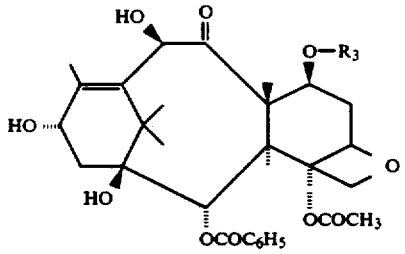

*wherein $R_3$ is a trialkylsilyl group in which each portion contains 1 to 3 carbon atoms.*

*14. A taxan derivative of the formula:*

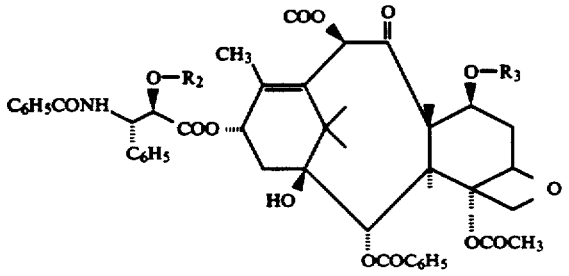

*wherein $R_2$ is a hydroxy-protecting group and $R_3$ is a trialkylsilyl group in which each portion contains 1 to 3 carbon atoms.*

*15. A taxan derivative according to claim 14 wherein $R_2$ is chosen from methoxymethyl, 1-ethoxyethyl, benzyloxymethyl, (β-trimethylsilylethoxy)methyl, tetrahydropyranyl and 2,2,2-trichloethoxycarbonyl.*

*16. A process for preparing taxol of the formula:*

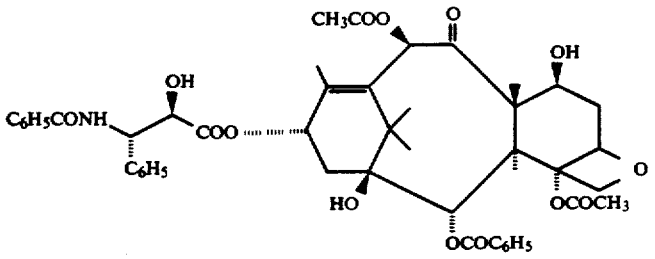

*comprising the following steps:*

*A. reacting a compound of the following formula:*

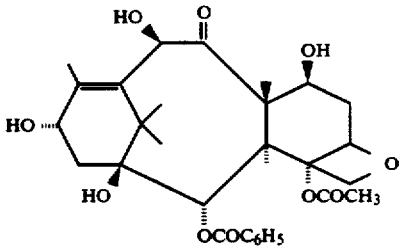

*with a halotrialkylsilane wherein each alkyl portion contains 1 to 3 carbon atoms, to form a compound of the following formula:*

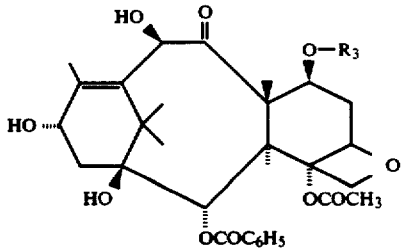

*in which $R_3$ is chosen from trialkylsilyl groups in which each alkyl portion contains 1 to 3 carbon atoms;*

*B. acetylating the compound so obtained with acetyl chloride to give a compound of the following formula:*

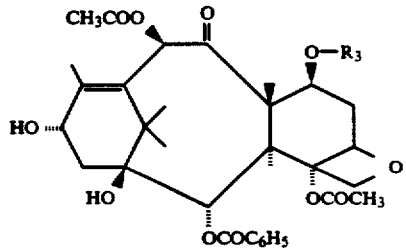

*C. esterifying the compound so obtained with a (2R, 3S) 3-phenylisoserine derivative of the general formula:*

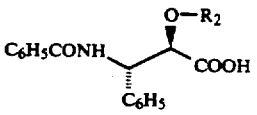
*in which $R_2$ is a hydroxy-protecting group; and*
*D. replacing both of the protecting groups $R_2$ and $R_3$ by hydrogen.*
*17. A process according to claim 16 in which $R_2$ is methoxymethyl, 1-ethoxyethyl, benzyloxymethyl, (β-trimethylsilylethoxy)methyl, tetrahydropyranyl or 2,2,2-trichloroethoxycarbonyl.*
* * * * *

UNITED STATES PATENT AND TRADEMARK OFFICE

CERTIFICATE OF CORRECTION

PATENT NO. : Re. 34,277

DATED : June 8, 1993

INVENTOR(S) : DENIS, et al.

It is certified that error appears in the above-identified patent and that said Letters Patent is hereby corrected as shown below:

Column 1, line 13, after [bacca-]tine, insert --III--.

Column 2, line 36, insert a dash ("-") between "(2R,3S)" and "3-phenylisoserine".

Column 3, line 18, delete "iospropylbenzene" and insert therefor --isopropylbenzene--;

Line 64, delete "aqueousal-" and insert therefor --aqueous-al--.

Column 5, line 57, delete "thinlayer" and insert therefor --thin-layer--.

Column 6, lines 27 and 61, delete "(2R, 3S)" and insert therefor --(2R,3S)--.

Column 7, line 9, delete "(1-ethoxy- ethyl)" and insert therefor --(1-ethoxyethyl)--.

Column 11, claim 12, delete the formula:

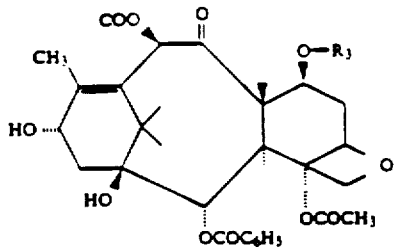

and insert therefor:

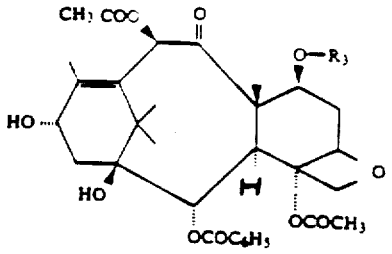

UNITED STATES PATENT AND TRADEMARK OFFICE

CERTIFICATE OF CORRECTION

PATENT NO. : Re. 34, 277

DATED : June 8, 1993

INVENTOR(S) : DENIS, et al.

It is certified that error appears in the above-identified patent and that said Letters Patent is hereby corrected as shown below:

Column 11, claim 13, delete the formula:

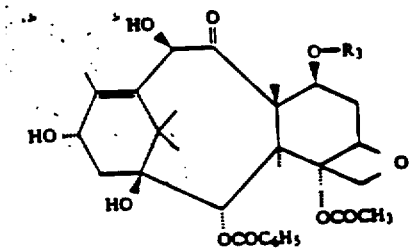

and insert therefor:

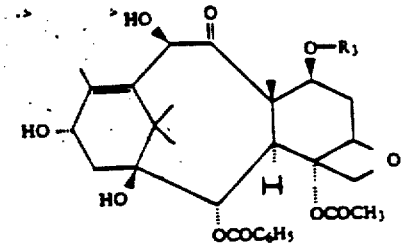

Column 11, claim 14, delete the formula:

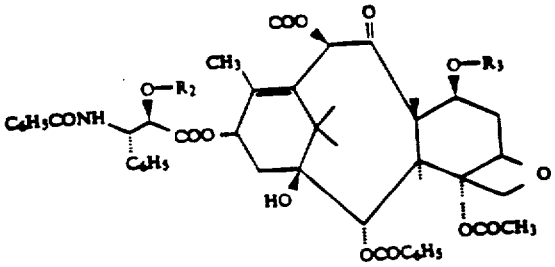

and insert therefor:

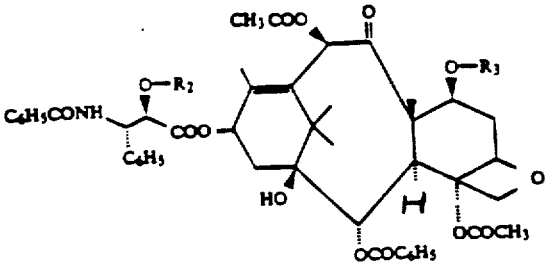

UNITED STATES PATENT AND TRADEMARK OFFICE

CERTIFICATE OF CORRECTION

PATENT NO. : Re. 34,277

DATED : June 8, 1993

INVENTOR(S) : DENIS, et al.

It is certified that error appears in the above-identified patent and that said Letters Patent is hereby corrected as shown below:

Column 12, line 2, delete "trichloethoxycarbonyl" and insert therefor --trichloroethoxycarbonyl--.

Column 12, claim 16, delete the formula:

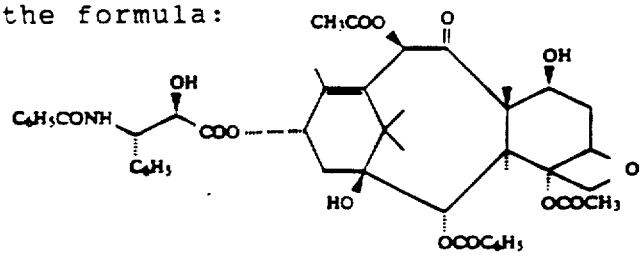

and insert the following:

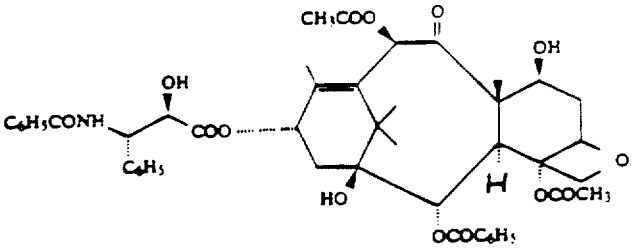

UNITED STATES PATENT AND TRADEMARK OFFICE

CERTIFICATE OF CORRECTION

PATENT NO. : Re. 34,277

DATED : June 8, 1993

INVENTOR(S) : DENIS, et al.

It is certified that error appears in the above-identified patent and that said Letters Patent is hereby corrected as shown below:

Column 12, claim 16, section "A.", delete the formula:

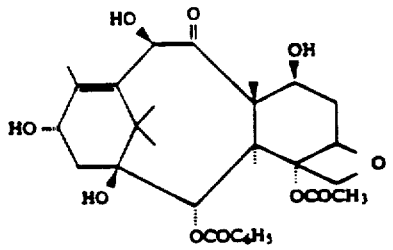

and insert therefor:

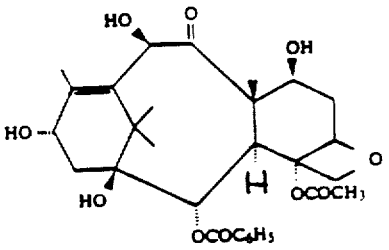

UNITED STATES PATENT AND TRADEMARK OFFICE

CERTIFICATE OF CORRECTION

PATENT NO. : Re. 34, 277

DATED : June 8, 1993

INVENTOR(S) : DENIS, et al.

It is certified that error appears in the above-identified patent and that said Letters Patent is hereby corrected as shown below:

Column 12, claim 16, section "A.", delete the formula:

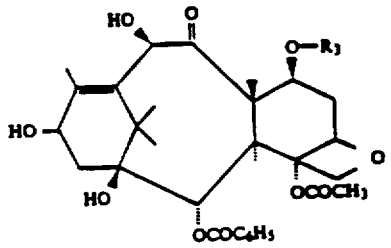

and insert therefor:

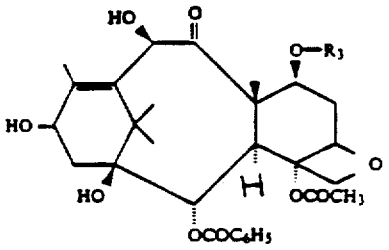

UNITED STATES PATENT AND TRADEMARK OFFICE

CERTIFICATE OF CORRECTION

PATENT NO. : Re. 34,277

DATED : June 8, 1993

INVENTOR(S) : DENIS, et al.

It is certified that error appears in the above-identified patent and that said Letters Patent is hereby corrected as shown below:

Column 12, claim 16, section "B.", delete the formula:

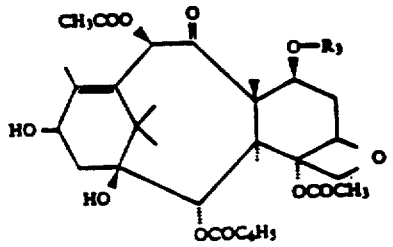

and insert therefor:

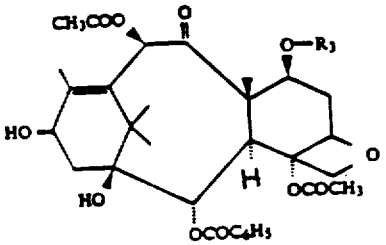

UNITED STATES PATENT AND TRADEMARK OFFICE

CERTIFICATE OF CORRECTION

PATENT NO. : Re. 34, 277

DATED : June 8, 1993

INVENTOR(S) : Denis, et. al.

It is certified that error appears in the above-indentified patent and that said Letters Patent is hereby corrected as shown below:

Column 12, line 67, insert a dash ("-") after "(2R,3S)".

Signed and Sealed this

Ninth Day of November, 1993

*Attest:*

*Attesting Officer*

BRUCE LEHMAN

*Commissioner of Patents and Trademarks*

UNITED STATES PATENT AND TRADEMARK OFFICE

CERTIFICATE OF CORRECTION

PATENT NO. : Re 34,277

DATED : June 8, 1993

INVENTOR(S) : DENIS et al.

It is certified that error appears in the above-identified patent and that said Letters Patent is hereby corrected as shown below:

On the cover page, Column 1, immediately before "Related U.S. Patent Documents", insert
-- Foreign Application Priority Data
Apr. 6, 1988[FR] France..... 8804512 --

Signed and Sealed this

Third Day of October, 1995

Attest:

Bruce Lehman

BRUCE LEHMAN

Attesting Officer

Commissioner of Patents and Trademarks